United States Patent [19]

Leemhuis

[11] 3,983,144

[45] Sept. 28, 1976

[54] NOVEL 11β-ALKYL STEROIDS OF THE ESTRANE SERIES

[75] Inventor: Johannes Antonius Joseph Leemhuis, Oss, Netherlands

[73] Assignee: Akzona Incorporated, Asheville, N.C.

[22] Filed: Dec. 4, 1974

[21] Appl. No.: 529,666

[30] Foreign Application Priority Data

Dec. 19, 1973 Netherlands .................. 7317358

[52] U.S. Cl. .................. 260/397.3; 260/397.5; 424/238
[51] Int. Cl.² .................................. C07J 1/00
[58] Field of Search .............. 260/397.3, 397.5

[56] References Cited
UNITED STATES PATENTS
3,032,469  5/1962  Gleason .................. 260/397.4

FOREIGN PATENTS OR APPLICATIONS
996,308  6/1965  United Kingdom .............. 260/397.5

Primary Examiner—Elbert L. Roberts
Attorney, Agent, or Firm—Francis W. Young; Philip M. Pippenger; Hugo E. Weisberger

[57] ABSTRACT

The present invention relates to novel steroids of the estrane series having the general formula I:

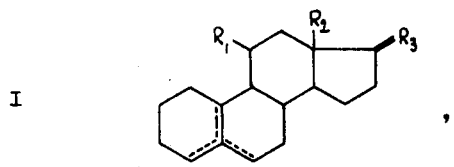

I wherein
$R_1$ and $R_2$ = an alkyl group having 1–4 carbon atoms,
$R_3$ = oxygen or $(\alpha P)(\beta Q)$, wherein
P = hydrogen or a saturated or an unsaturated alkyl group having 1–4 carbon atoms, and
Q = a free, esterified or etherified hydroxyl group, and
a double bond is present departing from carbon atom 5, and to the preparation thereof.

The compounds according to the invention possess very valuable anabolic, androgenic, estrogenic, anti-estrogenic, progestative, anti-progestative, ovulation-inhibiting and gonad-inhibiting properties and are furthermore of value owing to their peripheral anti-fertility activity.

6 Claims, No Drawings

NOVEL 11β-ALKYL STEROIDS OF THE ESTRANE SERIES

The invention relates to novel 11β-alkylsteroids of the estrane series and to the preparation thereof.

11β-Alkyl steroids of the estrane series are known. The 11β-alkyl steriods of the estrane series described in literature have an oxygen function at the position 3.

The present invention relates to novel 3-desoxy-11β-alkyl-estranes of the general formula I:

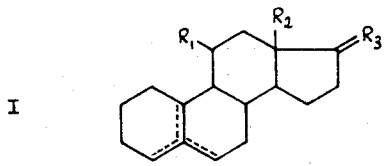

wherein
$R_1$ and $R_2$ = an alkyl group having 1-4 carbon atoms,
$R_3$ = oxygen or ($\alpha P$) ($\beta Q$), wherein
P = hydrogen or a saturated or an unsaturated alkyl group having 1-4 carbon atoms, and
Q = a free, esterified or etherified hydroxyl group, and
a double bond is present departing from carbon atom 5, and to the preparation thereof.

Of particular importance are the 3-desoxy-11β-alkyl-Δ⁴-estranes having an 11β-alkyl group of 2 or 3 carbon atoms.

The compounds according to the invention possess very valuable anabolic, androgenic, estrogenic, anti-estrogenic, progestative, anti-progestative, ovulation-inhibiting and gonad-inhibiting properties and are furthermore of value owing to their peripheral anti-fertility activity. The 17-oxo-compounds according to the invention are furthermore important starting products for the therapeutically valuable 17α-alkylated compounds of the invention. The 11β-methyl compounds of the invention have considerably stronger hormonal activities than the corresponding estrane compounds not carrying an 11β-methyl substituent. The 11β-propyl and 11β-butyl compounds of the invention have a hormonal profile, which is comparable to that of the 11β-methyl compounds, though the level of activity is lower. The 11β-ethyl compounds of the invention, such as for example 11β-ethyl-17α-ethinyl-Δ⁴-estren-17β-ol, have a very interesting hormonal profile characterized in that the progestational and estrogenic activities are relatively low and the ovulation-inhibiting and anti-progestational activities are relatively high. The 11β-isopropyl compounds have a hormonal profile which is comparable to that of the 11β-ethyl compounds, though the level of activity is somewhat lower.

The novel compounds can be produced by starting from a compound of the general formula II:

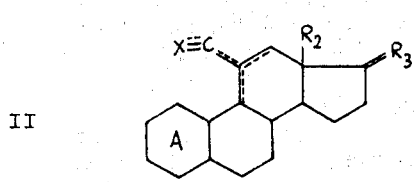

wherein $R_2$ and $R_3$ have the meanings given before;
a double bond is present departing from carbon atom 11;
X = ($R_5$) ($R_6$) when the double bond departing from carbon atom 11 is exocyclic, or (H) ($R_5$) ($R_6$) when the double bond departing from carbon atom 11 is endocyclic, and wherein $R_5$ and $R_6$ each are hydrogen or an alkyl group having 1-3 carbon atoms with the proviso that the total number of carbon atoms in $R_5$ and $R_6$ together is not more than 3;
and the partial formula comprising ring A and carbon atom 6 is

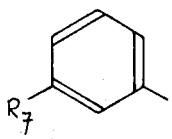 or

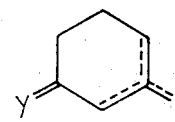

wherein
$R_7$ = a free, esterified or etherified hydroxyl group
Y = $H_2$, a temporarily protected or a non-protected oxo group or (H) (Z), wherein
Z = a free, esterified or etherified hydroxyl group, a halogen atom or a sulphonyloxy group and the partial formula having the substituent Y has a double bond departing from carbon atom 5.

In the starting compound of the general formula II the double bond departing from carbon atom 11 is reduced with hydrogen in the presence of a metal-catalyst, whereafter the aromatic ring A, if present, is reductively converted into a 3-oxo-Δ⁴ or a 3-oxo-Δ⁵⁽¹⁰⁾ group using the method of Birch followed by acid hydrolysis of the Δ²,⁵⁽¹⁰⁾-3-enolate; a 3-oxo-Δ⁴ group, if desired, is converted, via the 3-enol-acylate and a reduction of the double bond between the carbon atoms 3 and 4, into a 3-hydroxy-Δ⁵ group; any group present or still present at position 3 is removed according to methods known per se; and finally the substituents desired at position 17 and not yet present are introduced according to methods known per se.

The starting products of the general formula II can be produced by starting from the corresponding 11-oxo compounds and converting these into the 11,11-alkylidene-, 11-alkyl-Δ⁹⁽¹¹⁾- or 11-alkyl-Δ¹¹ steroids of the general formula II, according to known methods.

The conversion of the 11-oxo group into the 11,11-alkylidene group may be carried out, for example, by reacting the 11-oxo steroid with an organo-metal silane, for example trimethyl-silyl-alkyl-magnesium chloride or trimethyl-silylalkyl-lithium, and decomposing the resultant β-silyl-carbinol under the action of an acid or a base so that the 11,11-alkylidene steroid is formed. The reaction mechanism is described inter alia in an article of T.H. Chan c.s. in Tetrahedron Letters No. 14 (1970), pages 1137–1140.

Alternatively, the 11-oxo group may be converted into the 11,11-alkylidene group by means of Wittig reagent, for example triphenyl-alkylidene phosphorane which is prepared in situ from triphenylphosphine and an alkyl-halide with the aid of a suitable base, for example butyl lithium, ethyl magnesium bromide, dimethyl sodiumamide or dimsyl sodium.

As another alternative, the 11-oxo steroid may be converted into the 11,11-alkylidene steroid by an addition reaction with a lithium alkyl ether of thiophenol. The resultant 11-hydroxy-11-phenylthio-alkyl steroid, subsequent to esterification of the 11-hydroxy group to, for example, the 11-acetate or the 11-benzoate, can be reductively decomposed with the aid of lithium in liquid ammonia, the 11,11 -alkylidene steroid thus being formed (J.A.C.S. 94, No. 13 (1972) pages 4758–59).

The 11,11-alkylidene steroid can furthermore be produced by reacting the 11-oxo-steroid with a Grignard compound, for example methyl- or ethyl-magnesium bromide of the corresponding iodides or with an alkyl-metal compound such as methyl-lithium or ethyl-lithium, the resultant 11-alkyl-11-hydroxy steroid then being dehydrated or converted into the 11-alkyl-11-halogen steroid, especially the 11-alkyl-11-chlorosteroid or the 11-alkyl-11-bromo-steroid, this halosteroid being dehydrohalogenated. Dehydration can be carried out by treating the 11-alkyl-11-hydroxy-steroid with an acid, for example acetic acid or formic acid, in the presence of a trace of perchloric acid or a different dehydration agent, for example thionylchloride or phosphoroxychloride. For the dehydrohalogenation of the 11-alkyl-11-halogen steroid a suitable dehydrohalogenation agent is, for example, an alkali- or earth-alkali-metal carbonate, if necessary in the presence of an alkali-metal halide such as lithium bromide, or a different base such as collidine and potassium hydroxide.

The last-mentioned 11-alkylating method may also serve for producing starting products having an 11-alkyl-$\Delta^{9(11)}$ group or, as the case may be, an 11-alkyl-$\Delta^{11}$ group, since dependent on the reaction conditions in the dehydration and/or on the further structure of the steroid, a steroid having an exocyclic double bond or an endocyclic double bond or a mixture of these kinds can be formed. Thus, starting with an A-aromatic steroid predominantly the $\Delta$-alkyl-$\Delta^{9(11)}$ -compound is obtained and starting with a $\Delta^4$-3-oxo-steroid predominantly the 11,11-alkylidene compound is obtained.

For the subsequent reaction, the hydrogenation of the double bond departing from carbon atom 11 in order to form the 11$\beta$-alkyl steroids, it is not absolutely necessary for any mixture formed to be separated first.

The 11-alkyl-11-hydroxy steroids, from which the starting products having a double bond departing from carbon atom 11 can be obtained by dehydration, may, as an alternative, be prepared from the corresponding 11-oxo steroids by a reaction with an unsaturated alkyl-metal compound, for example, vinylmagnesium bromide or lithium acetylide, and catalytic hydrogenation of the resultant 11-alkenyl-11-11-hydroxy- or 11-alkynyl-11-hydroxy steroiod, for example the 11-vinyl-11-hydroxy or the 11-ethynyl-11-hydroxy steroid, to the 11-alkyl-11-hydroxy-steroid, for example the 11-ethyl-11-hydroxy steroid, said catalytic hydrogenation being performed for example with the aid of palladium on carbon.

In the above-mentioned methods of converting an 11-oxosteroid into a steroid of the general formula II may oxo group present in the steroid at other positions, for example, at the positions 3 and/or 17, are temporarily protected, for example by ketalization. The 3-or 17-oxo-group may be converted into the 3-or 17-ethylene ketal, for example by heating with ethylene glycol in the presence of p-toluene sulphonic acid. A 3-oxo group, if present, may, if desired, also be converted into the 3-thioketal group in order to protect it against the action of the reagents employed for the conversion of the 11-oxo group. This may be advantageous for producing the 3-desoxo compounds according to the invention, since after the conversion of the 11-oxo group and the reduction of the double bond departing from carbon atom 11, the 3-thioketal group can be split off by reduction. The latter reductive splitting off may, if desired, be performed simultaneously with the reduction of the double bond departing from carbon atom 11, for example with the aid of Raney nickel.

The reduction of the double bond departing from carbon atom 11 may be carried out in various ways, for example by hydrogenating the steroid concerned in alcoholic solution, for example in methanol or ethanol, with the aid of a palladium catalyst, for example 10% Pd on carbon or Pd on $BaSO_4$ or $BaCO_3$, or with the aid of Adams Catalyst (Pt).

Starting from 11-alkyl-$\Delta^{9(11)}$ steroids the reduction yields apart from the desired 11$\beta$-alkyl-9$\alpha$-H steroid also a slight quantity of the 11$\alpha$-alkyl-9$\beta$-H isomer, which can be separated from the 11$\beta$-alkyl-9$\alpha$-H steroid by crystallization. A mixture of said isomers is not formed when the 11,11-alkylidene compounds are used as starting products, so that in this respect 11,11-alkylidene steroids are preferred as starting materials.

The reduction, particularly of the 11,11-methylene compounds, can be advantageously carried out with the aid of Adams catalyst (Pt) in a mixture of tetrahydrofuran and an alcohol, such as methanol, ethanol, or isopropanol, in the presence of a small amount of acetic acid.

If the steroids according to the invention are produced by starting from the compounds of formula II having an aromatic A-ring, for example 3-hydroxy-11-methyl-$\Delta^{1,3,5(10),9(11)}$-estratetraen-17-one 3-methylether or 3-hydroxy-11,11-methylene-$\Delta^{1,3,5(10)}$-estratrien-17-one 3-methylether 17-ethylene-ketal, and reducing the double bond departing from carbon atom 11, the aromatic A-ring is reduced thereafter to the $\Delta^{2,5(10)}$-3-enolether group by means of the Birch reduction method (reduction with an alkalimetal in liquid ammonia). The enolether can be easily hydrolysed either by diluted strong acid with heating to the 3-oxo-$\Delta^4$ compound or by mild acid at room temperature to the 3-oxo-$\Delta^{5(10)}$ compound.

The 3-oxo group is subsequently removed by thioketalization, for example by a reaction with a mercaptan or dithiol in the presence of $BF_3$ or the etherate thereof or in the presence of $ZnCl_2$, and by reductive splitting off of the thioketal group, for example by treatment with an alkali-metal, preferably lithium, in the presence of liquid ammonia or a lower aliphatic primary amine such as methylamine or ethylamine.

Finally, the substituents desired at position 17, as far as not yet present, are introduced in a way known per se.

If the starting substance is a 3-oxo compound of formula II or the 3-ketal- or 3-thioketal thereof, the 3-oxo- or 3-thioketal group is split off subsequent to the reduction of the double bond departing from carbon atom 11 and (if required) to the hydrolysis of the 3- ketal group by the method already described above, after which, if necessary, the substituents desired at position 17 are introduced.

If the starting substance is a 3-desoxy compound of formula II, i.e. Y = H$_2$, it is only necessary, after the reduction of the double bond departing from carbon atom 11, to introduce the substituents desired at position 17, as far as they are not yet present.

If the starting substance is a $\Delta^4$-compared of formula II the reduction of the double bond departing from carbon atom 11 yields besides the desired 11$\beta$-alkyl-$\Delta^4$ compound also the corresponding 4,5-dihydro compound which, of course, adversely affects the yields of the desired compound. However, starting from the 3-ketal of a 3-oxo-11,11-alkylidene-$\Delta^4$ steroid according to formula II, for example the 3-ketal of 11,11-methylene-17$\beta$-hydroxy-$\Delta^{6^4}$-estren-3-one or the 3,17-diketal of 11,11-methylene-$\Delta^4$-estrene-3,17-dione, the exocyclic double bond can surprisingly be selectively hydrogenated with the aid of Adams catalyst (Pt) in an alcoholic solution, for example, in ethanol or in a mixture of isopropanol and tetrahydrofuran, in the presence of a small amount of acetic acid. In this reduction the double bond, now in 5-6-position due to the 3-ketalisation is not affected.

After the reduction the 3-ketal group and, if present, the 17-ketal group is converted by acidic hydrolysis into the corresponding oxo group(s), after which the 3-oxo grup is split off in the manner already described above and, if necessary, the substituents desired at position 17 are introduced. It will be clear that owing to the smaller number of reaction steps this method is preferred to that in which the starting substance is a compound having an aromatic A-ring.

If the starting substance is a compound of formula II having a 3-hydroxy group which may be etherifield or esterified, then after the reduction of the double bond departing from carbon atom 11 and, as the case may be, after hydrolysis of the 3-ether- or 3-ester-group, the 3-hydroxy group is converted into the 3-halo-or 3-sulphonyloxy group by halogenation or sulphonylation. Subsequently, the 3-substituent is reductively off by treatment with an alkali metal in liquid ammonia, a lower aliphatic amine such as methylamine or an alcohol such as ethanol or by treatment with an alkali-metal aluminium hydride, for example LiAlH$_4$.

The halogenation may take place, for example, with phosphortrichloride, phosphorpentachloride, thionylchloride or the corresponding bromides.

Sulphonylation may be carried out by reaction the 3-hydroxy steroid with a sulphonic acid or a functional derivative thereof such as methane sulphonic acid, benzene sulphonic acid, toluene sulphonic acid or the corresponding acid chlorides thereof.

As an alternative, first the 3-hydroxy group may be converted into the 3-halo or the 3-sulphonyloxy group and subsequently the double bond departing from carbon atom 11 is reduced, after which the 3-halo or the 3-sulphonyloxy group is reductively split off.

Last-mentioned reduction may, if desired, be performed simultaneously with the reduction of the double bond departing from carbon atom 11.

A $\Delta^5$-compound according to the invention may be obtained from an intermediate 3-oxo-11$\beta$-alkyl-$\Delta^4$-compound by converting the latter into the 3-enol-acylate, reducing the double bond in 3-4-position and hydrolysing the 3-acylate, after which the 3$\beta$-hydroxy group can be split off in the manner described before and the substituents in 17-position can be introduced, if not yet present.

The substituent at position 13 is already present in the starting steroid and may be a methyl-, ethyl-, propyl-, isopropyl- or a butyl-group, preferably a methyl- or ethyl- group.

The alkyl group at position 11 may be a methyl-, or ethyl-, propyl-, isopropyl-, butyl- or an isobutyl-group.

The starting products for the preparation of the 11$\beta$-alkyl steroids according to the invention may already have the 17-substituents as indicated in formula I, but these substituents may, as an alternative, be introduced as yet at the end. A saturated or unsaturated alkyl group in 17$\alpha$-position is preferably introduced after the reduction of the double bond departing from carbon atom 11 and the required reactions for forming the 3-desoxo-$\Delta^4$-, -$\Delta^5$- or -$\Delta^{5(10)}$-group.

The introduction of a saturated or an unsaturated alkyl group at position 17 is carried out by reacting the 11$\beta$-alkyl-17-oxo steroid, which may be obtained by the oxidation of the corresponding 17$\beta$-hydroxy compound by the Oppenauer method or with chromium trioxide, with a metal derivative of a saturated o an unsaturated, substituted or non-substituted, aliphatic hydrocarbon, if necessary followed by a further conversion of the side chain thus introduced.

The metal derivative may be a Grignard compound, for example the magnesium bromide of the hydrocarbon concerned or an alkyl lithium compound. A particular form of the condensation reaction for producing the 17$\beta$-hydroxy-17$\alpha$-alkynyl compounds consists in that the 17-oxo steroid is reacted with a triple unsaturated hydrocarbon in the presence of an alkalimetal or an alkalimetal compound, for example an alkalimetal amide or -alcoholate or with an alkalimetal or earthalkalimetal compound of a triple unsaturated hydrocarbon.

The 17-alkylation may, as an alternative, be carried out in two stages by first producing via a condensation reaction the 17$\beta$-hydroxy-17$\alpha$-alkynyl compound and then converting the latter by reduction, for example with the aid of hydrogen in the presence of a catalyst such as nickel or Pd/BaSO$_4$, into the corresponding 17$\alpha$-alkenyl- or 17$\alpha$-alkyl compound.

The hydrocarbon radical, which may be present in the final products at position 17, may be a methyl-, ethyl-, propyl-, butyl-, isopropyl-, vinyl-, propenyl-, isopropenyl-, allyl-, methallyl-, ethynyl-, propynyl-, propargyl-, butynyl-, butadienyl-, butadiynyl-, propadienyl-, or butenynyl-radical.

An ester group, if any, in the final products at position 17 may be derived from an inorganic acid such as phosphoric acid or from a saturated or unsaturated organic carboxylic acid having 1 to 18 carbon atoms. The ester production may be carried out by a method known per se, for example by reacting the 17$\beta$-hydroxy steroid with the acid concerned or a functional derivative thereof such as the anhydride or the halide of by reacting the reaction product obtained by the condensation of the 17-oxo steroid with a metal derivative of an unsaturated hydrocarbon radical without preliminary hydrolysis with the acid concerned or a functional derivative thereof. Esterification may, as an alternative, be performed by reacting the steroid with a carboxylic acid anhydride such as acetic acid anhydride in the presence of 4-dimethylamino-pyridine, preferably also in the presence of a tertiary amine such as trimethylamine.

Examples of organic carboxylic acids, from which the ester group can have been derived, are: formic acid, acetic acid, propionic acid, butyric acid, valeric acid, caprinic acid, caproic acid, enanthic acid, caprylic acid, pelargonic acid, undecylic acid, lauric acid, tridecylic acid, myristic acid, pentadecylic acid, oleic acid, palmitinic acid, stearic acid, adamantane-carboxylic acid, trimethylacetic acid, diethyl-acetic acid, cyclohexane-carboxylic acid, cyclopentyl-propionic acid, cyclohexyl-butyric acid, cyclohexyl-propionic acid, undecylenic acid, benzoic acid, phenyl-acetic acid, phenyl-propionic acid, phenyl-butyric acid, phenoxyacetic acid, acetyl-acetic acid, malonic acid, succinic acid, glutaric acid, pimelinic acid and tartaric acid.

Ether groups, which may be present at position 17 in the final products and, if present, have been introduced in a way usual for such groups, may be derived from an aliphatic, aromatic araliphatic or heterocyclic hydrocarbon. Examples of such ether groups are the methyl ether-, butyl ether-, cyclopentyl ether-, tetrahydropyranyl ether-, cyclohexyl ether- and vinylethyl ether-group.

The compounds obtained in accordance with the invention can, usually subsequent to mixing with auxiliaries and, if desired, with other active constituents, be administered parenterally or orally in the form of suspensions, emulsions or solid pharmaceutical shapes such as tablets, pills and dragees.

The following examples serve to illustrate the practice of the present invention.

EXAMPLE I a. 3 g of 11-methyl-$\Delta^{1,3,5(10),9(11)}$-estratetraene-3,17$\beta$-diol 3-methylether dissolved in 360 ml of methanol was reduced by hydrogen at room temperature with the aid of 0.3 g of Pd/C (10%) as a catalyst. After 1 mol. equivalent of hydrogen had been absorbed, the catalyst was removed by filtration and the filtrate was evaporated to dryness. Crystallization from ether-hexane yielded the 11$\beta$-methyl-$\Delta^{1,3,5(10)}$-estratriene-3,17$\beta$-diol 3-methylether.

b. 2 g of 11$\beta$-methyl-$\Delta^{1,3,5(10)}$-estratriene-3,17$\beta$-diol 3-methylether was dissolved in 40 ml of tetrahydrofuran and this solution was added to a solution containing 160 ml of liquid ammonia, 100 ml of tetrahydrofuran and 14 ml of tertiary butylalcohol. Whilst stirring, 1 g of sodium dissolved in 40 ml of liquid ammonia was added to said mixture. After stirring for 1 hour, 20 ml of methanol was added and the solution was evaporated to dryness. The residue was purified by trituration, washing with water and drying. The resultant 11$\beta$-methyl-$\Delta^{2,5(10)}$-estradiene-3,17$\beta$-diol 3-methylether was heated for 40 minutes in 300 ml of methanol and 60 ml of 4N hydrochloric acid to just below the reflux temperature. After cooling, the mixture was neutralized with a solution of sodium bicarbonate. The mixture was extracted with ether and the extract was dried and subsequently evaporated. The purification of the residue with ether-hexane yielded the 11$\beta$-methyl-17$\beta$-hydroxy-$\Delta^4$-estren-3-one.

c. To a solution of 6.5 g of 11$\beta$-methyl-17$\beta$-hydroxy-$\Delta^4$-estren-3-one in 72 ml of methanol 7 ml of ethane dithiol and 7 ml of BF$_3$-etherate were successively added at 0°C. The reaction mixture was stirred at this temperature for one hour, poured into water and extracted with methylene chloride. The extract was washed to neutral with water and evaporated in vacuo. The residue (8.3 g of crude 11$\beta$-methyl-17$\beta$-hydroxy-$\Delta^4$-estren-3-one 3-ethylene-dithioketal) was dissolved in 44 ml of dry tetrahydrofuran. This solution was added to a solution of 4.8 g of sodium in 185 ml of liquid ammonia at −40°C in an N$_2$ atmosphere. After stirring for 30 minutes at −40°C the excess sodium was decomposed with 33 ml of ethanol and the ammonia was evaporated off. The residue was diluted with water. The resultant precipitate was filtered off and dried in vacuo. In this way 5.9 g of crude 11$\beta$-methyl-$\Delta^4$-estren-17$\beta$-ol was obtained.

d. To a solution of 5.9 g of crude 11$\beta$-methyl-$\Delta^4$-estren-17$\beta$-ol 7.2 ml of 8N CrO$_3$ was added dropwise in 10 minutes at −10°C. After a reaction period of 20 minutes at −10°C the excess CrO$_3$ was removed by a sodium bisulphite solution. Whilst distilling off acetone in vacuo, the reaction mixture was diluted with water and the resultant precipitate was filtered off. After purification with the aid of column chromatography and crystallization from acetone 4.2 g of 11$\beta$-methyl-$\Delta^4$-estren-17-one were obtained.

EXAMPLE II

In a similar manner as described in Example I (a)–(c) 11-ethyl-, 11-propyl-, 11-isopropyl- and 11-butyl-$\Delta^{1,3,5(10),9(11)}$-oestratetraene-3,17$\beta$-diol 3-methylether were converted into 11$\beta$-ethyl-$\Delta^4$-estren-17$\beta$-ol, 11$\beta$-propyl-$\Delta^4$-estren-17$\beta$-ol, 11$\beta$-isopropyl-$\Delta^4$-estren-17$\beta$-ol and 11$\beta$-butyl-$\Delta^4$-estren-17$\beta$-ol, from which by chromic acid oxidation in a manner as described in Example I d), 11$\beta$-ethyl-$\Delta^4$-estren-17-one, 11$\beta$-propyl-$\Delta^4$-estren-17-one, 11$\beta$-isopropyl-$\Delta^4$-estren-17-one and 11$\beta$-butyl-$\Delta^4$-estren-17-one were obtained.

EXAMPLE III a. 2.4 g of 11,11-methylene-$\Delta^5$-estrene-3,17-dione 3,17-diethylene-ketal were hydrogenated with hydrogen in a solution of 36 ml of isopropanol, 36 ml of tetrahydrofuran and 1 ml of acetic acid with the aid of 0.2 g of Adams catalyst. After the absorption of 1 mol of hydrogen per mol of steroid the catalyst was filtered off and the filtrate evaporated to dryness. The residue was dissolved in 48 ml of acetone and hydrolysed with 0.2 ml of concentrated hydrochloric acid for one hour at room temperature.

After processing and crystallization from methylene chloride-ether 1.9 g of 11$\beta$-methyl-$\Delta^4$-estrene-3,17-dione were obtained.

In a manner as described in Example I (c) 11$\beta$-methyl-$\Delta^4$-estrene-3,17-dione was converted via the 3-ethylene-dithioketal compound into 11$\beta$-methyl-$\Delta^4$-estren-17$\beta$-ol from which by oxidation with chromic acid 11$\beta$-methyl-$\Delta^4$-estren-17-one was obtained.

b. In a similar manner 11$\beta$-ethyl-$\Delta^4$-estren-17$\beta$-ol and 11$\beta$-ethyl-$\Delta^4$-estren-17-on were obtained from 11,11-(E)-ethylidene-$\Delta^5$-estrene -3,17-dione 3,17-diethyleneketal.

EXAMPLE IV a. 150 mg of 3-hydroxy-11,11-methylene-$\Delta^{1,3,5(10)}$-estratrien-17-one 3-methylether were hydrogenated in 10 ml of methanol with 50 mg of Pd/C (10%) as a catalyst. After filtration of the catalyst the filtrate was evaporated to dryness and crystallized from ether In this way 3-hydroxy-11$\beta$-methyl-$\Delta^{1,3,5(10)}$-estratrien-17-one 3-methylether was obtained.

b. In a similar manner as described in Example I (b)–(d) 3-hydroxy-11$\beta$-methyl-$\Delta^{1,3,5(10)}$-estratrien- 17-one 3-methylether was converted into 11β-methyl-Δ⁴-estren-17β-ol and 11β-methyl-Δ⁴-estren-17-one.

c. In a similar manner as described in Example I (b) 311β-methyl-Δ¹,³,⁵⁽¹⁰⁾-estratrien-17-one 3-methylether was reduced to the corresponding Δ²,⁵⁽¹⁰⁾-compound, which was subsequently treated with acetic acid. The obtained 11β-methyl-17β-hydroxy-Δ⁵⁽¹⁰⁾-estren-3-one was converted in a similar manner as described in Example I (c) and (d) into 11β-methyl-Δ⁵⁽¹⁰⁾-estren-17β-ol and 11-methyl-Δ⁵⁽¹⁰⁾-estren-17-one, respectively.

EXAMPLE V 1.5 g of 11,11-methylene-Δ⁵-estren-17-one was hydrogenated in a solution of 15 ml of methanol and 15 ml of tetrahydrofuran with 0.15 g of Adams catalyst. After processing and crystallization 1.1 g of 11β-methyl-Δ⁵-estren-17-one were obtained.

EXAMPLE VI a. 2.5 g of 11,11-methylene-18-methyl-Δ⁵-estrene-3β,17β-diol diol 17 -benzoate were hydrogenated in a solution of 25 ml of methanol and 25 ml of etrahydrofuran with 0.25 g of Adams catalyst. After processing and crystallization 1.9 g of 11β,18-dimethyl-Δ⁵-estrene-3β,17β-diol 17-benzoate were obtained.

b. 1.9 g of this 11β,18-dimethyl-compound were dissolved in 5 ml of methylene chloride, after which 2 ml of thionyl chloride were added dropwise. The mixture was kept at room temperature for 3 hours, poured out into glacial water and extracted with methylene chloride. The extract was washed with a sodium bicarbonate solution and subsequently chromatographed on silicagel, yielding 3β-chloro-11β,18-dimethyl-Δ⁵-estren-17β-ol 17-benzoate.

c. A solution of 1.8 g of 3β-chloro-11β,18-dimethyl-Δ⁵-estren-17β-ol 17-benzoate in 36 ml of absolute ether was added to a solution of 1.8 g of lithium in 51 ml of liquid ammonia. The mixture was stirred for 2 hours, after which 6 ml of 96% ethanol were added. The ammonia was evaporated and the residue was diluted with water. The aqueous mixture was extracted with ether and the extract was washed with water, dried and evaporated to dryness in vacuo. Chromatography of the dry residue on silicagel yielded 11β,18-dimethyl-Δ⁵-estren-17β-ol.

EXAMPLE VII a. A solution of 2.9 g of 11β-methyl-Δ⁴-estren-17-one in 12 ml of dry tetrahydrofuran was added to a potassium acetylide solution in tetrahydrofuran obtained by passing acetylene through a stirred suspension of 12 g of potassium t-butylate in 100 ml of dry tetrahydrofuran. After stirring for 2 hours at a temperature between 0°C and 5°C the reaction mixture was acidified with 2N H₂SO₄, poured out into water and extracted with chloroform. The extract was washed with water and evaporated to dryness. Chromatography of the residue on silicagel and crystalization from pentane yielded 2.4 g of 11β-methyl-17α-ethinyl-Δ⁴-estren-17β-ol.

b. By replacing the potassium acetylide solution in Example VIII (a) by a sodium vinylacetylide solution obtained by the reaction of vinyl-acetylene with sodium amide in liquid ammonia, 11β-methyl-Δ⁴-estren-17-one yielded in a similar manner 11β-methyl-17α-butyn-1,3-enyl-Δ⁴-estren-1β-ol.

c. In a similar manner as described in Example VII (a) 11β-ethyl-Δ⁴-estren-17-one, 11β-propyl-Δ⁴-estren-17-one, 11β-isopropyl-Δ⁴-estren-17-one, 11β-butyl-Δ⁴-estren-17-one and 11β-methyl-Δ⁵⁽¹⁰⁾-estren-17-one were converted into 11β-ethyl-17α-ethinyl-Δ⁴-estren-17β-ol, 11β-propyl-17α-ethinyl-Δ⁴-estren-17β-ol, 11β-isopropyl-17α-ethinyl-Δ⁴-estren-17β-ol, 11β-butyl-17α-ethinyl-Δ⁴-estren-17β-ol and 11β-methyl-1α-ethinyl-Δ⁵-estren-17β-ol, respectively.

d. By reduction with the aid of prehydrogenated Pd on barium sulphate (5% Pd) the 17α-ethinyl compounds obtained in Examples VII (a) and (c) were selectively hydrogenated to the corresponding 17α-vinyl- and upon a further reduction to the corresponding 17α-ethyl compounds.

EXAMPLE VIII a. A solution of 0.94 g of 11β-ethyl-17α-ethinyl-Δ⁴-estren-17β-ol in 10 ml of dry pyridine was added to 5 ml of acetic anhydride. After stirring for 3 hours at reflux temperature, the reaction mixture was poured out into ice water and extracted with diethylether. The extract was washed with water and evaporated to dryness. By chromatography of the residue on silicagel 0.6 g of 11β-ethyl-17α-ethinyl-⁴-estren-17β-ol 17β-acetate were obtained.

b. In a similar manner the 17β-hydroxy-compounds obtained in Example VII were converted into the 17β-esters, derived from acetic acid, valeric acid, enanthic acid, lauric cid, phenylpropionic acid and succinic acid, wherein with the exception of acetic acid, the acid chloride instead of the acid anhydride was employed.

EXAMPLE IX

A solution of 0.9 g of 11β-methyl-Δ⁴-estren-17-one in 12 ml of tetrahydrofuran was added to an allyl-magnesium bromide solution in ether. After 2 hours of stirring at room temperature the reaction mixture was poured out into ice water plus sulphuric acid. By processing after extraction and chromatography on silicagel 0.7 g of 11β-methyl-17α-allyl-Δ⁴-estren-17β-ol were obtained.

In a similar manner 11β-methyl-Δ⁵-estren-17-one was converted into 11β-methyl-17α-allyl-Δ⁵-estren-17β-ol.

By replacing the allyl-magnesium bromide solution in the process described above by an ethyl-lithium solution the following compounds were obtained:
11β-methyl-17α-ethyl-Δ⁴-estren-17β-ol and
11β-methyl-17α-ethyl-Δ⁵-estren-17β-ol.

In a similar manner 0.5 g of 11β,17α-dibutyl-Δ⁴-estren-17β-ol in the form of an oil were obtained from 1.2 g of 11β-butyl-Δ⁴-estren-17-on with the aid of butyl-lithium in diethylether and 0.4 g of 11β-methyl-17α-isopropyl-Δ⁴-estren-17β-ol were obtained from 1.1 g of 11β-methyl-Δ⁴-estren-17-one with the aid of isopropyl-lithium in diethylether.

By esterification the 17β-hydroxy compounds mentioned in this Example were converted into the 17β-esters, derived from acetic acid, propionic acid, phenyl-propionic acid, caprinic acid and undecylenic acid, respectively.

By etherification of the 17β-hydroxy compounds the 17-methyl-, 17-butyl-, 1-vinyl-ethyl- and the 17-tetrahydropyranyl-ethers were obtained.

EXAMPLE X

A solution of 3.2 g of 3-(1'-ethoxy-ethoxy)-prop-1-yn in 30 ml of tetrahydrofuran were added to a solution of ethyl-magnesium bromide prepared from 2.65 g of ethyl bromide and 0.54 g of magnesium in 40 ml of tetrahydrofuran. The mixture was boiled for 5 minutes in a reflux cooler and subsequently stirred at room temperature for 2 hours. To the resultant solution of 3-(1'-ethoxy-ethoxy)-prop-1-ynyl-magnesium bromide a solution of 2.85 g of 11β, 18-dimethyl-Δ⁴-estren-17-one in 30 ml of tetrahydrofuran was added. After refluxing for 7.5 hours the reaction mixture was cooled to room temperature and poured out into ice water. The aqueous mixture was neutralized with acetic acid and subsequently extracted with methylene chloride. The extract was washed, dried and evaporated to dryness. By chromatography of the residue on silicagel 1.4 g of 11β,18-dimethyl-17α-3'(1''-ethoxy-ethoxy)-prop-1'-ynyl-Δ⁴-estren-17β-ol were obtained, which were dissolved in 35 ml of ether. At room temperature this solution was added to a suspension of 1.4 g of LiAlH₄ in 35 ml of ether. The mixture was refluxed for 2.5 hours, cooled to room temperature and poured out into ice water. After acidification with 10% hydrochloric acid, the product was isolated by extraction with methylene chloride. Chromatography on silicagel yielded 0.7 g of 11β,18-dimethyl-17α-propadienyl-Δ⁴-estren-17β-ol.

By esterification the 17β-acylates were obtained, derived from formic acid, butyric acid, phenyl-acetic acid and malonic acid.

EXAMPLE XI

In the manner described in Example III, 11,11-methylene-18-methyl-Δ⁵-estrene-3,17-dion 3,17-diethylene ketal was converted into 11β,18-dimethyl-Δ⁴-estren-17-one. In the manner described in Example VII the latter compound was converted into 11β,18-dimethyl-17α-ethinyl-Δ⁴-estren-17β-ol.

EXAMPLE XII

A solution of 0.24 g of 11β-butyl-Δ⁴-oestren-17β-ol in 2 ml of dry pyridine was added to 0.5 ml of acetic anhydride. After standing for 15 hours at room temperature the mixture was poured out into ice water and extracted with methylene chloride. The extract was evaporated. 0.27 g of 11β-butyl-Δ⁴-estrene-17β-ol 17β-acetate were obtained. By using phenylpropionic acid chloride instead of acetic anhydride, 11β-butyl-Δ⁴-estrene-17β-ol 17β-phenylpropionate was obtained.

EXAMPLE XIII 16 g of 11β-methyl-17α-ethinyl-Δ⁴-estren-17β-ol were reacted to the corresponding 17α-acetyl compound in a mixture of 500 ml of toluene and 250 ml of ethanol with the mixture of 10 g HgO and 17.5 ml of concentrated sulphuric acid in 250 ml of ethanol and 175 ml of water for 30 minutes at 60°C. Processing by extraction, followed by chromatography on silicagel yielded 4.4 g of 11β-methyl-17α-acetyl-Δ⁴-estrene-17β-ol.

Treatment of this 17α-acetyl compound with 6 ml of trimethylsilyl chloride in a mixture of 50 ml of dimethylacetamide and 6 ml of pyridine for 3 hours at 20°C, followed by processing by extraction yielded the corresponding 17β-trimethylsilyl ether. This silyl ether in 150 ml of pyridine and 30 ml of toluene was reacted with Wittig reagent (36 g of triphenylmethylene phosphorane and 32.4 ml of butyllithium (20%) in hexane) at 80°C for 4.5 hours.

Processing by extraction and chromatographic purification yielded 11β-methyl-17α-isopropenyl-Δ⁴-estren-17β-ol 17β-trimethylsilyl ether. The ether group was hydrolysed by treating the product in acetone (100 ml) with hydrochloric acid (0.3 ml 38%) at 20°C for 1¼ hour.

Extraction and crystallization from ether-methanol yielded 1.2 g of 11β-methyl-17α-isopropenyl-Δ⁴-estren-17β-ol.

What is claimed is:

1. Novel steroids of the estrane series having the general formula I:

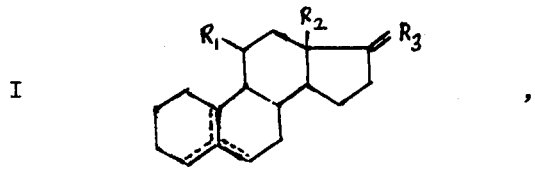

wherein
R₁ and R₂ = an alkyl group having 1–4 carbon atoms,
R₃ = O or (α P) (β Q), wherein
 P = H or a saturated or an unsaturated alkyl group having 1–4 carbon atoms, and
 Q = hydroxy, acyloxy derived from an organic carboxylic acid having 1–18 carbon atoms, or an ether group selected from the group consisting of saturated or unsaturated alkoxy having 1–4 carbon atoms, cycloalkoxy having 5 or 6 carbon atoms and tetrahydropyranyloxy and
a double bond is present departing from carbon atom 5.

2. Novel estrane compounds having the general formula III

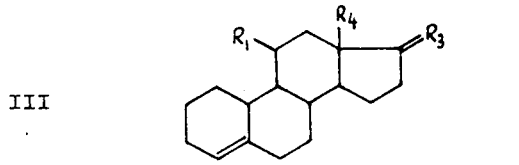

wherein
R₁ and R₃ have the meanings as indicated in claim 1, and
R₄ = methyl or ethyl.

3. Novel estrane compounds having the general formula III of claim 2, wherein R₃ and R₄ have the meanings as indicated in claim 2 and R₁ is an alkyl group having 2 or 3 carbon atoms.

4. Novel estrane compounds having the general formula III of claim 2, wherein R₃ and R₄ have the meanings as indicated in claim 2 and R₁ is ethyl.

5. 11β-Ethyl-17α-ethinyl-Δ⁴-estren-17β-ol and its 17β-acylates.

6. Pharmaceutical preparations containing one or more of the compounds of claim 1 as active constituent.

* * * * *